United States Patent
Bradley (10) Patent No.: US 6,653,135 B1
(45) Date of Patent: Nov. 25, 2003

(54) DYNAMIC PROTEIN SIGNATURE ASSAY

(75) Inventor: Brian P. Bradley, Ellicott City, MD (US)

(73) Assignee: University of Maryland, Baltimore, MD (US)

( * ) Notice: Subject to any disclaimer, the term of this patent is extended or adjusted under 35 U.S.C. 154(b) by 66 days.

(21) Appl. No.: 09/661,399

(22) Filed: Sep. 13, 2000

(51) Int. Cl.[7] .................. A61K 49/00; G01N 33/567; G01N 33/569; G01N 33/53; G01N 33/543

(52) U.S. Cl. .................. 435/377; 424/9.1; 424/9.2; 435/7.22; 435/7.31; 435/7.32; 435/7.95; 435/29; 435/34; 435/35; 435/39; 435/70.1; 435/71.1; 435/243; 435/244; 435/245; 435/375; 435/390

(58) Field of Search .................. 424/9.1, 9.2; 435/7.22, 435/7.31, 7.32, 7.95, 29, 34, 35, 39, 70.1, 71.1, 243, 244, 245, 375, 377, 390

(56) References Cited

PUBLICATIONS

Anderson et al. 1998. Electrophesis. 19:1853–61.*
Bradley et al., 1994. Environ. Tox. and Chem. 13(7):1043–1050.*
Blackstock et al. 1999. Trends Biotech. 17:121–127.*
Blom et al. 1992. Applied and Environ. Micro. 58(1):331–333.*
Bradley et al. 1993. Marine Environ. Res. pp. 85–88.*
Bradley et al. Amer. Soc. Testing and Materials. STP1306, Philadelphia (1996).*
Anderson, N.L and N.G. Anderson, Proteome and proteomics: new technologies, new concepts and new words, Electrophoresis, 19:1853–61 (1998).

Arnold, R.J. and Reilly, J.P. Fingerprint matching of *E. coli* strains with matrix–assisted laser desorption/ionization time–of–flight mass spectrometry of whole cells using a modified correlation approach, Rapid Commun. Mass Spectrom., 12:630–6 (1998).

Blackstock et al., Proteomics: quantitative and physical Proteins, Trends Biotech, 17:121–7 (1999).

Blom, et al., Unique and Overlapping Pollutant Stress Proteins of *Escherichia coli.*, Applied Environmental Microbiology, 58(1):331–334(1992).

Bradley et al., Chemical Abstracts, Abstract No. 21161v, vol. 113 (1989).

(List continued on next page.)

*Primary Examiner*—Lynette R. F. Smith
*Assistant Examiner*—JaNa Hines
(74) *Attorney, Agent, or Firm*—Piper Rudnick LLP; Steven B. Kelber (57) ABSTRACT

An assay to determine the specific expression and suppression of proteins in response to a stressor is disclosed. An organism exposed to a stressor, including disease caused by exposure to, e.g., a parasite, or a substance suspected of causing an adverse effect, is assayed to determine a first set of proteins expressed and a second set of proteins suppressed in response to the stressor. The amount of each protein expressed and the amount of each protein suppressed can be statistically analyzed to determine which proteins are most useful in diagnosing the stressor. A protein profile for a first stressor can be compared to protein profiles for a second stressor, a third stressor, etc. A distinct protein expression signature (PES) for the first stressor can be identified by determining subsets fo proteins expressed and/or suppressed only in response to the first stressor. The quantified set of proteins can then be used as a template for comparison to the protein expression signature of a biological sample to determine if the organism has been exposed to the stressor.

9 Claims, 8 Drawing Sheets

PUBLICATIONS

Bradley, B.P. and J.B. Ward, Detection of a major stress protein using a peptide antibody, Mar. Environ. Res. 28:471–475 (1989).

Bradley, B.P. and J.B. Ward. A molecular mechanism of adaptation in an estuarine copepod., Neth. J. Sea Res., 30:1–6 (1989).

Bradley, B.P. 1992. Are the stress proteins specific indicators of exposure or effect?, Mar. Environ. Res., 34:85–88 (1992).

Bradley, B.P., Brown, D.C., Lamonte, T.N., Boyd, S.N. and O'Neill, M.C., Protein patterns and toxicity identification using artificial neural networks in Biomarkers and Risk assessment, Amer. Soc. Testing and Materials STP1306, Philadelphia (1996).

Bradley, B.P., C.M. Gonzalez, J.A. Bond and B.E. Tepper, Complex mixtures analysis using protein expression as a qualitative and quantitative tool, Environ. Tox. and Chem., 13:1043–50 (1994).

Claydon, M.A. Davey, S.N. Edwards–Jones, V. and Gurdon, P.E., The rapid identification of intact microorganisms using mass spectrometry, Nature Biotechnol., 14:1584–6 (1996).

Craig et al., Is hsp 70 the cellular thermometer?, Trends Biochem. Sci., 16:135–140 (1991).

Haag, A.M., Taylor, S.N., Johnston, K.H. and Cole, R.B., Rapid identification and specification of Haemophilus bacteria by matrix–assisted laser desorption/ionization time–of–flight mass spectrometry, J. Mass Spectrom, 33:750–6 (1996).

Hahn, G.M. and Li, C.G., Thermotolerance, thermoresistance, and thermosensitization, Stress Proteins in Biology and Medicine, Cold Spring Harbor Laboratory Press, Cold Spring Harbor, NY, pp. 79–100 (1990).

Herbert et al., Two–Dimensional Electrophoresis: The State of the Art and Future Directions, Proteome Research: New Frontiers in Functional Genomics, Spring–Verlag, Berlin (1997).

Hightower, L. E., Heat–shock proteins, chaperones and proteotoxicity, Cell, 66:191–197 (1991).

Humphrey–Smith, S.J., Cordwell and W. Blackstock, Proteome research: complementarity and limitations with respect to the RNA and DNA worlds, Electrophoresis, 18:1217–42 (1997).

Jellum et al., Two–Dimensional Electrophoresis for Determining Toxicity of Environmental Substances, Analytical Chemistry, 55: 2340–2344 (1993).

Kultz et al., Differences in Protein Patterns of Gill Epithelial Cells of the Fish Gillichthys mirabilis After Osmotic and Thermal Acclimation, J. Comp. Physiol., 166: 88–100 (1996).

Lindquist et al., The heat–shock proteins, Ann. Rev. Genet., 22:631–677 (1988).

McCarthy et al., Biological markers of environmental contamination, Biomarkers of Environmental Contamination, Lewis, Boca Raton, Florida, pp. 3–14 (1990).

Nover, L., Heat Shock Response, Chapters 1, 2 and 6, CRC, Boca Raton, Florida (1991).

Nover, L., et al. Heat Shock Response of Eukaryotic Cells, Chapters 2 and 3, (1984).

Parsell, D.A., J. Taulien and S. Lindquist. 1993. The role of heat–shock proteins in thermotolerance. Phil. Trans. R. Soc. Lond. B 339:279–286.

Ringwood, A.H., D.E. Conners and J. Hoguet, The Effects of Natural and Anthropogenic Stressors on Lysosomal Destablization in Oysters, Crassosrra virginica, Marine Ecology Progess Series (1998).

Sanders, B. M., Stress proteins in aquatic organisms: An environmental perspective, Crit. Rev. Toxicol., 23:49–75 (1993).

Stegmann et al., Molecular responses to environmental contamination: Enzyme and protein systems as indicators of chemical exposures and effects, Biomarkers: Biochemical, Physiological and Histological Markers of Anthropogenic Stress, Lewis, Boca Raton, Florida, pp. 235–310 (1992).

Van Bogelen, R.A., P.M. Keley and F.C. Neidhardt, Differential induction of heat shock, SOS and oxidation stress regulations and accumulation of nucleotides in *E. coli.*, J. Bacteriol. 169:26–32 (1987).

Welch, W.J. How cells respond to stress, Sci. Am., 268:56–64 (1993).

Welch, W.J., Heat shock proteins functioning as molecular choperones: Their roles in normal and stress cells, Phil. Trans. R. Soc. Lond B, 339:327–333 (1993).

Williams et al., Introduction to the Proteome, In Proteome Research: New Frontiers in Functional Genomics, Springer–Verlag, Berlin (1997).

Winston, G.W., M.N. Moore, I. Staatsburg and M.A. Kirchin, Decreased Stability of Digestive Gland Lysosomes from the Common Mussels Alytilus edulis L., In Vitro Generation of Oxygen–Free Radicals, Arch. Environ. Contam. Toxicol., 21:401408 (1991).

* cited by examiner

DYNAMIC PROTEIN SIGNATURE ASSAY

BACKGROUND OF THE INVENTION

1. Field of the Invention

The present invention relates to methods and diagnostic kits for determining environmental quality, i.e., internal or external conditions that may have an effect on an organism. In particular, the invention relates to methods and diagnostic kits for determining stress induced on an organism through alterations or degradation in environmental quality. More specifically, organisms in the environment are exposed to a stressor, e.g., disease, substances to treat disease, or any other substance that may have an adverse effect on the organism, and a protein expression signature for the stressor, i.e., those proteins uniquely expressed and those proteins uniquely suppressed in response to the stressor, is determined. Protein expression signatures for one or more stressors may then be used to identify exposure to a stressor or class of stressors present in an environment.

2. Background of the Prior Art

It is desirable to provide a system that cannot only provide quantitative measurement of stressor(s), but qualitative information as well, such as the type of stressor causing the adverse effect on the organism.

Many prior art assays are confined to lethal assays. That is, laboratory animals are generally exposed to concentrations of a stressor. Presumptive evidence of no adverse effect exists if the animal or organism survives exposure.

A drawback to such systems is the fact that acute lethal affects are rarely observed. Rather, in general, adverse conditions arise slowly, which corresponds to a gradual increase in or long term exposure to a stressor. A stressor eventually, lethal responses are observed and identified. However, at this point it is generally too late to remedy. In any event, the stressor has no gross observable effect (mortality) on the organism at the time of the test. In general, such assays serve only to confirm the investigator's suspicion that there was decreased environmental quality, and that the disappearance of the organism was not due to some alternative, unexplained natural cause.

Other prior art assays, although not lethal, require extended exposure (and expense) or sophisticated procedures and/or equipment.

The present inventor had previously developed a sublethal assay that determines the presence of a stressor in an environment (see U.S. Pat. Nos. 5,149,634 and 5,250,413, the entire contents of which are incorporated herein by reference) and an assay that determines proteins synthesized by *Daphia magna* after exposure to mixtures of a cationic polyamide epichlorhydrin adduct (Kymene) and a combined assortment of water-extractable substances from chemi-thermal-mechanical pulp (see Bradley et al. (1994)). The assay of U.S. Pat. Nos. 5,149,634 and 5,250,413 involve the identification and correlation of the presence of at least three different stress proteins to a specific environmental chemical pollutant.

The present inventor has determined that although the assay disclosed in U.S. Pat. Nos. 5,149,634 and 5,250,413 is effective, there remains a need for more rapidly and accurately: (1) detecting the presence of change in environmental quality below lethal levels; (2) providing quantitative information regarding the presence of a stressor; (3) providing qualitative information, concerning the identity of the stressor; and (4) providing a simple measurement to determine the health of an organism (e.g., animal, human or other biota).

SUMMARY OF THE INVENTION

The present invention is directed to a method of determining environmental quality, i.e., internal or external conditions that may have an adverse effect on an organism, including disease, substances to treat disease or any other substance that may have an adverse effect on the organism. Specifically, a single organism or organisms are exposed to a stressor and a protein profile for the stressor, i.e., those proteins expressed and those proteins suppressed in response to exposure to the stressor, is determined. The organisms can either be exposed singly or as a population of two or more. A protein profile for an individual organism, or for a population of organisms, is thus obtained. The above steps are then repeated for a second stressor, a third stressor, etc., until a protein profile is obtained for all of the stressors that need to be monitored (or pathologies that need to be followed). Each protein profile is compared to the others to determine proteins distinct for a given stressor. These distinct proteins (present and absent) comprise the protein expression signature for each stressor. Some shock proteins, or stress proteins, are expressed and other shock proteins are suppressed in virtually all organisms in a response to stress. The term stress herein is widely used to include any internal or external condition that may have an effect on an organism. Stressors may be biological, due to diseases or parasites for example, and have an adverse effect on the organism. These ubiquitous shock proteins are expressed (or suppressed) by the organism in response to the stressor well in advance of the point at which lethal quantities are encountered and in advance of outward manifestations of disease or other adverse conditions. The stressor need not be chemical in nature. Any condition which places the organism under stress but does not necessarily kill the organism, thereby forcing it to respond to sublethal conditions, may be a stressor.

Some shock proteins are highly conserved across species and genus lines. Thus, the determination of protein expression signatures provides a ready method for sampling diverse environments and for the use of diverse organisms (from the environment or the laboratory). Investigation has shown that the expression (or suppression) of shock proteins by the organisms in question is related to the concentration or amount of stressor. Thus, the amount of stress protein expressed (or suppressed) by the organism will give a direct indication of the degree of severity of the stressor. Additionally, a variety of organisms may be sampled, to determine whether or not the stressor is toxic, both to the test animal and other organisms that may be of interest, such as domestic animals, humans and other plants and animals. Moreover, different stressors induce (or suppress) different types of shock proteins. By determining the set of shock protein(s) expressed and suppressed, it is possible to rapidly and accurately identify the stressor encountered. Accordingly, steps can be taken to eradicate or correct the stressor.

DETAILED DESCRIPTION OF THE INVENTION

Adaptation to stress includes changes in protein expression. These changes may be due to transcriptional, posttranscriptional and posttranslational modifications. Jellum et al. (1983); Bradley et al. (1994); Stegmann et al. (1992); Welch, (1993). Protein expression varies specifically with analyte and with the concentration of a stressor. Bradley et al. (1996). As the concentration increases, the biologically significant impact also increases.

Protein expression changes with the state of development, the tissue and the internal and external environmental conditions of an organism. The entire protein complement of an organism, i.e., the proteome, is increasingly being studied to identify key molecules involved in normal physiological pathways, as well as in disease. Williams et al. (1997). There is growing evidence that sets of proteins up- and down-regulate in response to a stressor. Blom et al. (1992); Jellum et al. (1983); Bradley (1996); Kultz et al. (1996). Recently, techniques have been developed to analyze large numbers of proteins simultaneously to discern subtle changes in protein expression. Herbert et al. (1997).

Protein expression and other subcellular responses in organisms can be used in environmental quality testing. McCarthy et al. (1990); Sanders et al. (1993); Stegmann et al. (1992). Increased and decreased levels of key proteins, sometimes referred to as "stress proteins," may be used as quantitative and qualitative indexes of environmental quality. There is a rich literature on stress proteins, including their better known subset, the heat shock proteins. Craig et al. (1991); Hightower (1991); Lindquist et al. (1988). They are not only indicators but also seem to have roles, possibly related, in thermotolearance and as molecular chaperones. Hahn et al. (1990); Parsell et al. (1993); Welch et al. (1993).

The quantitative response in these proteins, a 70,000 Da family of proteins in particular, is well documented. Bradley et al. (1989); Bradley et al. (1992). However, the potential of classes of proteins induced and suppressed by particular stressors as specific indicators of stress has not been recognized.

The entire protein complement of the genome, known as the proteome, can now be analyzed for changes associated with specific treatments. The methods are collectively known as proteomics. Andersen et al. (1998). Protein expression can now be analyzed in parallel to mRNA expression. Thus, gene expression can be examined at two levels. Gene activity and relative abundance of proteins are not always closely related and post-transitional modifications are not seen at all in studies including only RNA expression. Humphrey-Smith et al. (1997).

In addition to being complementary to genomics, proteomics allows specific assays of stressors and even identification of organisms based on protein expression signatures. Bradley et al. (1994 and 1996) and Claydon et al. (1996). The thousands of proteins available include many specific to class of analyte, to individual chemical and even to concentration of the chemical. The chemical may be a contaminant, a toxin, an internal signaling compound and includes any substance that may have an adverse effect on an organism.

An additional virtue of proteomics is the ability to investigate protein sequences and functions using mass spectrometry. Only recently has it been possible to ionize molecules as large as proteins. Mann et al. (1995). Now, the data from mass spectrometry can be entered into one of the many databases available to determine homologies with known proteins. The functions of key proteins may then be identified.

There are many applications of proteomics. To date, the major emphasis for its use has been in the drug industry (discovery and therapeutics). In medical diagnostics, the application has been to find new protein markers for diseases. In environmental proteomics, it has been established that specific proteins are induced by different chemical stressors. Further use of proteomics could be beneficial by providing early warning of problems, monitoring health of indigenous organisms, identifying toxicants in mixtures (as well as the toxin-producing organisms), identifying the toxic components of a complex effluent, identifying toxicants in substances used to treat organisms, testing pathogenicity, diagnosing disease and identifying genes predisposed to disease states.

The present inventor has found specificity in protein expression for all compounds, organisms, and stressors examined. With the use of proprietary software, proteins that differ from treatment to treatment can readily be isolated and key proteins usable in simple diagnostic tests based on immunological or other specific reactions can be identified. Combinations of such key proteins can provide accurate assessment of any condition of interest, whether related to organism health or to potential environmental hazard.

The Genome Project, which has permitted the identification of a vast number of genes and proteins has fueled great improvement in techniques for separating, identifying and characterizing proteins. In particular, measuring molecular mass very precisely and analyzing very small quantities of protein with electrospray and desorption mass spectrometry, coupled with the large protein databases, have vastly increased the power of protein analysis.

There is evidence that strains and species can be identified using proteome analysis. Haag et al. (1996) and Arnold et al. (1998). This has been done in pure cultures. The present inventor has done the equivalent with chemical mixtures. In principle, strains of organisms could be identified by stable proteins, by toxin secreted (hot response) and by pathogenicity. The present inventor has shown a general response in a heat shock protein to exposure to *P. marinus*, the well known oyster parasite. According to the literature, physiological states (pathogenicity in particular) of the organism should be distinguishable as well.

There has been considerable experience in the determination in protein expression in response to heavy metals. Bradley et al. (1994) and (1996). Metals that cause physiological stress from among those in the ambient mixture can be identified.

The method of the invention relies on the observation that in response to stress, an extraordinarily wide variety of organisms express a relatively narrow range of proteins not otherwise expressed and suppress a relatively narrow range of proteins not otherwise suppressed.

Nover (1984) describes a wide variety of inducers of shock proteins or stressors, and the observed response in a variety of organisms, including vertebrates, ciliates and Drosophila. The assay disclosed in Nover is a sublethal one. Thus, it is not necessary for stress to build to toxic levels or for observable symptoms to appear in order to use the assay. The Nover assay is not specific. However, it is valuable in early detection of situations which might later become lethal.

These shock proteins, in addition to being expressed (or suppressed) by virtually all eukaryotes, are highly conserved. Thus, certain shock proteins, widely observed in a variety of organisms are expressed or suppressed only in response to stress. Thus, the expression of specific shock proteins and the suppression of other shock proteins can be assayed for in organisms exposed to an environment suspected of containing a stressor. The presence of the specific shock proteins and the absence of other shock proteins confirms the presence of a stressor, as these specific proteins are not normally expressed and the other shock proteins are not normally suppressed by the organism. The amount of specific shock protein expressed and/or amount of the other shock protein suppressed correlates directly with the amount or stressor present. The specific shock proteins observed and/or the absence of the other shock proteins gives some indication as to the type of stressor or the reason for the poor health of an organism.

To carry out the method of the invention, the organism may either be cultivated under controlled conditions (e.g., in a laboratory) and then exposed to the environment or taken from the environment directly. In the latter situation, the normal or standard (basal) level for protein expression in the organism should first be obtained to permit comparison.

By using the method of the invention, extremely low levels of a stressor or other distress of the organism, can be rapidly and accurately detected. The relative health of the organism can also be determined or monitored.

Virtually any organism naturally present in the environment can be evaluated using the method of the invention. Preferred organisms are those that are easily raised in the laboratory and dominant in the environment. As an example, copepods, for an aquatic environment, such as Chesapeake Bay, are a highly suitable subject. Other aquatic subjects include mysid shrimp, decapod larvae and bivalve larvae. These organisms are particularly suitable because of the ease with which they may be raised and maintained in the laboratory. Virtually all organisms appear to induce or suppress shock proteins in response to a wide variety of stressors, and accordingly, are suitable subjects. If desired, even higher mammals and humans may be used as test species (see Example 3 below). In the case of higher mammals and humans, where damage from sampling is not acceptable, blood samples, tissue samples or similar harmless sampling may be taken.

According to the invention, a combination of proteins unique to a stressor is isolated by current methods of analysis. These include separation of proteins in two dimensions (2D) and isolation of those proteins induced or suppressed only by the stressor of interest. Blackstock et al. (1999), the entire contents of which are incorporated herein by reference, discloses methods of protein separation and identification. These proteins comprise the protein profile for the stressor of interest. Protein expression signatures (PES) are derived from the profiles as described earlier.

The proteins in the PES are then weighted either by discriminant function analysis or by using artificial neural networks (ANNs), both well-known techniques, and those most important in diagnosis are identified.

This subset of the original PES are followed through several levels of stress to identify those whose expression changes systematically, up or down. A single index of specific stress can be developed, which increases with stress, by using weighted amounts of proteins present.

Protein expression can be used to diagnose stress and to determine functional response to stress. A specific assay will not include all proteins important in the resistance of the organism to stress, rather the method will distinguish functional from purely diagnostic proteins.

According to the invention, proteins from a sample that has been exposed to a stressor are extracted, separated by charge and by mass and visualized in 2D maps by staining. These 2D displays are digitized and presented to software for image analysis. Composite images are made for each treatment (exposure) or class of treatments and comparisons of interest among the composite images are made. Proteins consistently present or consistently absent are then isolated. Those of particular diagnostic use are excised and sequenced directly or are digested into peptide fragments and analyzed by mass spectrometry. At this point, these key proteins are identified for possible function. Specific assays based on antibodies or other specific binding agents may be prepared.

The present invention permits the following:

(1) Isolation of key proteins to identify specific stressors using discriminant analysis and ANNs;

(2) Identification of key proteins which change systemically with concentration of stressor; and (3) Combination of the relative amounts of key proteins into a quantitative, dynamic index to assess the impact of a particular stressor (chemical, pathogen, etc.).

Uses of the present invention include the following:

(1) Diagnosis of specific toxicity in organisms;

(2) Early warning of disease, thus permitting effective treatment or perhaps prevention;

(3) Diagnosis of disease in humans, plants or animals (similar to current diagnostic methods, which rely on single protein markers);

(4) Confirmation of recovery from disease or from toxicity, wherein the absence of signature proteins provides the confirmation;

(5) Regular health monitoring of humans, plants or animals, wherein protein profiles are periodically compared and PES associated with pathologies is observed;

(6) Toxicity testing for specific analytes in mixtures, wherein test organisms with PES for the analyte of interest are used;

(7) Augment or replace chronic toxicity testing by predicting toxicity at an earlier time;

(8) Define limits of impact at a contaminated site using either indigenous species or test organisms such as bacteria or earthworms;

(9) Post facto diagnosis of cause of death using a degraded protein signal;

(10) Incorporation of reporter genes into bacteria (or other sentinel organisms) to indicate the induction or repression of genes specific to a stressor of interest;

(11) Therapy based on replacement or augmentation of protective or reactive proteins specifically induced by a stressor, for example, in compromised skin; and (12) Measurement of the potential of a population to resist or to recover from pollution stress, by physiological (short-term) or genetic (long-term) adaptation.

(13) Identification of multiple drug targets, weighted in importance.

The present invention can be incorporated into lab and field testing units. The latter may be based on simple visual assessment, electronic readout or remote sensing. The former, and the latter as well, could include multiple arrays of specific capture molecules.

The present invention will be described in the following non-limiting examples.

EXAMPLES

Example 1

As discussed above, methods are now available to study the proteome, which is the entire complement of proteins produced by an organism. According to an embodiment of the present invention, proteome analysis is used to isolate protein expression signatures (PES). Specific PES were isolated in *Mytilus edulis*, mussels from the Baltic Sea, that had been subjected in the laboratory to treatment (1) with copper (70 ppb), (2) with Aroclor 1248 (1 ppb), (3) to lowered salinity, and (4) to lowered salinity plus copper. Protein expression signatures, including those proteins induced and those proteins suppressed by exposure, were isolated for each treatment group.

Eight blue mussels *Mytilus edulis* 2–3 cm in size were collected from a natural population 3M deep. Ambient salinity and temperature were a salinity of 6.3 ppt and a temperature of 7° C. The mussels were put in tanks for acclimation for 24 hours at the same temperature and salinity as collection. Mussels were moved to 5 liter exposure tanks and exposed for 7 days to one of five treatment regimes: 70 ppb copper, 1 ppb Aroclor 1248, salinity of 3 ppt, 70 ppb copper combined with lower salinity (3 ppt) and a control at ambient conditions. Water was changed every other day and continuously aerated. At the end of the 7 day exposure, mussels were removed from the shell and flash frozen in liquid nitrogen before being freeze dried for later analysis.

Freeze dried whole body tissue was mechanically homogenized in cold buffer containing phenyl-methylsulfonyl fluoride and dithiothreotol (PMSF and DTT, protease inhibitors) and tris buffer pH 5.5. After mechanical homogenization, samples were boiled to further break down cells, and cellular debris was removed by centrifugation (13000×g for 5 min). Total protein concentration was determined using methods based on the Bradford method (Biorad).

The supernatant containing the soluble protein fraction was separated using two dimensional electrophoresis (Biorad Miniprotean II™). The gels were scanned to TIFF images using an EPSON Expression 636 flatbed scanner. Gels from each treatment were compared for changes in pattern and key components using Medical Electrophoresis Analysis Interactive Expert System (MELANIE II™) 2D analysis software (Biorad) and data compiled using a database developed by this laboratory. Composite gels were produced from each treatment set and compared to one another. Proteins uniquely present (induced (expressed)) or absent (suppressed) in each treatment were identified. Those present or absent in all the original component gels were included in the protein expression signature (PES) for each treatment.

Analysis of the separated proteins allowed identification of unique protein expression signatures for each stressor used. The PES (induced and suppressed) for Aroclor 1248 included 23 proteins. An expression signature of 23 proteins was found for copper treatment. Five of the proteins in this signature were identified in organisms treated with copper and lowered salinity simultaneously. Lowered salinity caused a PES of 26 proteins, 10 of these were also identified in organisms treated with copper in conjunction with lowered salinity. (See Table 1 and FIG. 1).

The three stressors produce three distinct protein expression signatures (PES), based on the presence or absence of proteins. In some cases a signature based on binary digits may not be sufficient. In such cases, the analysis by identifying quantitative changes in protein abundance should be continued. Experiments including all possible mixtures of the stressors should be used. Those proteins contributing most to the variation among treatments can then be identified.

TABLE 1

The number of proteins found specifically induced (present) and suppressed (absent) for each stressor: copper, Aroclor 1248, lowered salinity, copper and lowered salinity.

| Unique Induction | | Unique Suppression | |
|---|---|---|---|
| Aroclor 1248 | 5 proteins | Aroclor 1248 | 18 proteins |
| Copper | 13 proteins | Copper | 10 proteins |
| Salinity | 17 proteins | Salinity | 9 proteins |
| Copper/Salinity shared signal | | Copper/Salinity shared signal | |
| Copper | 3 proteins | Copper | 2 proteins |
| Salinity | 4 proteins | Salinity | 6 proteins |

Example 2

Lysosomal stability is a useful indicator of cellar damage. Lysosomes are cellular organelles important in the nutrition, tissue repair and turnover of cellular components. They also accumulate and sequester xenobiotics and metals. Winston et al. (1991); Ringwood et al. (1998). The sequestration of chemicals and metals in the lysosome can lead to damage of the lysosomal membrane. The "leaking" of the lysosome can result in increased cell damage and toxicity. Lowe et al. (1994).

According to another embodiment of the invention, protein expression changes together with lysosomal damage, a cellular impact in *Mytilus edulis* exposed to a range of concentrations of copper, are assessed; quantitative lysosomal stability ratio based on the area of haemolymph cell lysosomes from *Mytilus edulis* is developed; a dose response in lysosomal stability and protein expression is identified; and changes in protein expression is related to cell damage using lysosomal damage as an indicator.

Protein expression and lysosomal stability were observed in *Mytilus edulis* exposed to 0, 20, 40, 60, and 80 ppb copper sulfate for 24 hours in a static exposure system. Haemolymph was removed from each mussel and analyzed for lysosomal damage using the Neutral Red retention assay expressed as the ratio of lysosomal size to cell area, the lysosomal destabilization ratio (LDR). Gill tissue from these same individuals was dissected, homogenized and the proteins extracted and then separated using two-dimensional gel electrophoresis. Two-dimensional protein maps from each concentration were analyzed using MELANIE II™ 2D gel analysis software (Biorad). Lysosomal damage increased with each dosage, with LDRs ranging from 0.18±0.01 at 0 ppb copper sulfate to 0.32±0.11 at 80 ppb copper sulfate. Orthogonal comparisons showed that the control, 20 ppb and 40 ppb classes together differed significantly (p<0.05) from the 60 ppb and 80 ppb classes together. Specific protein expression signatures were identified at each dosage.

Nine *Mytilus edulis* ranging from 3–5 cm were collected from mussel growing flats in Tenants Harbor, Me. Mussels were acclimated in 40 gallon tanks with a salinity of 30 ppb at 4° C. before they were placed in acute exposure chambers. After acclimation, mussels were exposed to 0 ppb, 20 ppb, 40 ppb, 60 ppb, and 80 ppb copper (as $CUSO_4$), for 24 hours in three replicate flasks.

Gill tissue previously flash frozen in liquid nitrogen was mechanically homogenized in cold buffer containing phenyl-methylsulfonyl fluoride and dithiothreotol (PMSF and DTT, protease inhibitors). Cellular debris was removed by centrifugation (13000×g for 5 min). Total protein concentration of the supernatant containing the soluble protein fraction was determined using the Bradford method.

Total protein (30 ug) was separated using two dimensional electrophoresis, separating first based on the isoelectric focusing point with a pH range from three to ten followed by separation by molecular weight (Biorad Miniprotean II™) (Bradley (1990); Bradley (1993); Bradley et al. (1994)). Polyacrylamide gels (12%) from nine individuals per treatment group were scanned using an EPSON Expression 636 flatbed scanner. Spots on each gel were detected and compared using Medical Electrophoresis Analysis Interactive Expert System (MELANIE II™) 2D analysis software (Biorad). Composite gels for each treatment group were compiled using spots found on 75% of the component gels and compared to one another. Spots found on the control composite and not on the treatment composite were not detectable in gels from treated groups and were considered absent. Those spots detectable on the treatment composites only were considered present. Each spot of interest, present or absent, on the treatment composites was identified on all original gels from a treatment group before being considered part of the protein expression signature.

Lysosomal stability was measured using a Neutral Red Retention assay modified from Ringwood et al. (1998) and Svedsen et al. (1995). Approximately 0.3–0.5 ml haemolymph was removed from the anterior adductor muscle with a syringe containing 0.3–0.5 ml temperature adjusted (4° C.) $Ca^{2+}/Mg^{2+}$ Free Saline (CMFS). Haemolymph was placed on microscope slides where cells were allowed to adhere before 8 mg/ml Neutral Red Stain and a cover slip were added followed by a 45 minute incubation in a humidity chamber. (Ringwood et al. (1998); Svedsen et al. (1995)). Slides were then viewed at 400× magnification using a Nikon Labophoto Microscope and a MOS color video camera attachment. For each slide, the first six cells encountered with a discernible lysosome were saved as a computer PICT files. A ratio of lysosomal damage was then computed using NIH Image software and compared across treatment groups using orthogonal ANOVA. The ratio of lysosomal damage (Lysosomal Destabilization Ratio (LDR)) consists of the area taken up by the lysosome divided by the area of the total cell. A cell with maximal lysosomal damage has a LDR of 1, while a cell with minimal lysosomal damage has a ratio approaching zero.

Over this time, there was no change in attachment (byssus formation) of feeding (clearance rate) behavior in the organisms. The amount of lysosomal destabilization or damage increased with each dosage from 0.18±0.01 at 0 ppb $CuSO_4$ to 0.32±0.11 at 80 ppb $CuSO_4$ (see Table 2). The LDRs were not significantly different among the 0 ppb, 20 ppb and 40 ppb concentrations of $CuSO_4$ (p>0.05). The LDR for the lowest dosages collectively differed from 60 ppb and 80 ppb $CuSO_4$ (p<0.05) (see Table 2).

Figure 1A:
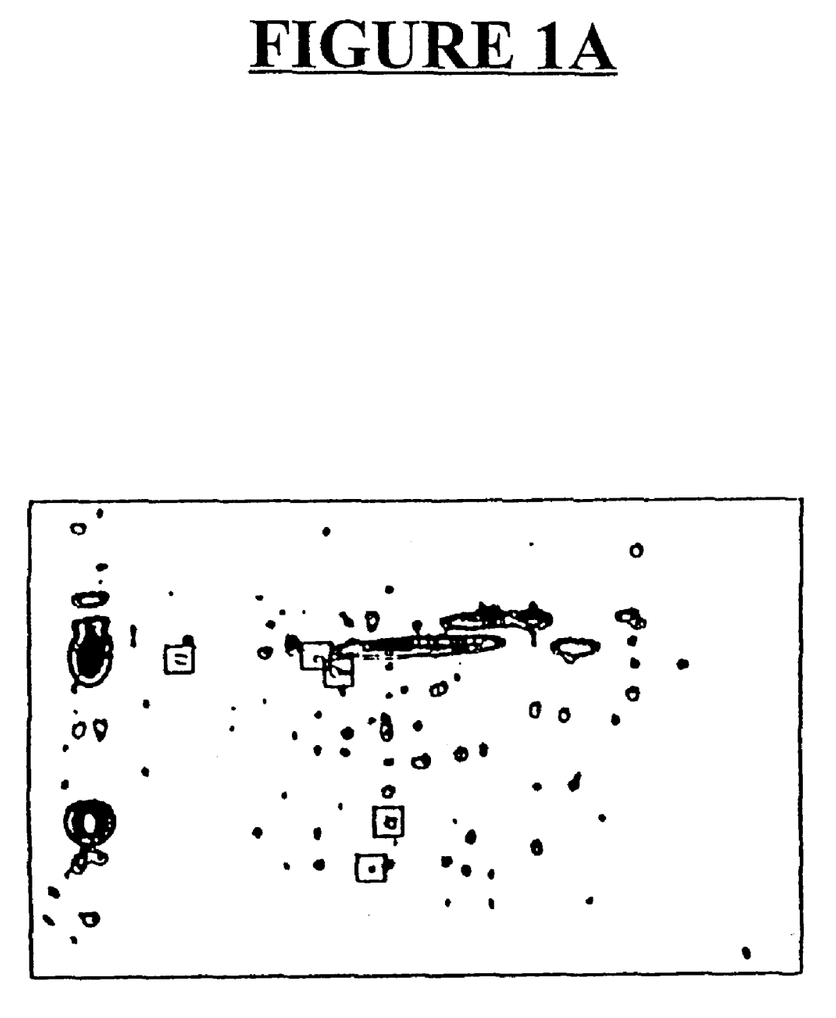
FIGS. 1(A) to 1(F) show two-dimensional gel separation of whole body homogenate proteins from *Mytilus edulis* exposed to copper, lowered salinity, copper and lowered salinity, and Aroclor 1248. Composite gels were produced using spots found on 75% of constituent gels. Key proteins induced (expressed) (absent on control gel) are denoted with circles and suppressed (absent on treatment gel) are denoted with squares. (A) composite gel with proteins induced by 1 ppb Aroclor 1248; (B) control composite with proteins suppressed by 1 ppb Aroclor 1248; (C) composite showing proteins induced by 70 ppb copper; (D) control composite showing proteins suppressed by 70 ppb copper alone; (E) salinity composite with proteins induced by lowered salinity (6 to 3 ppt); and (F) control composite with proteins suppressed only by lowered salinity (6 to 3 ppt).
Figure 1B:
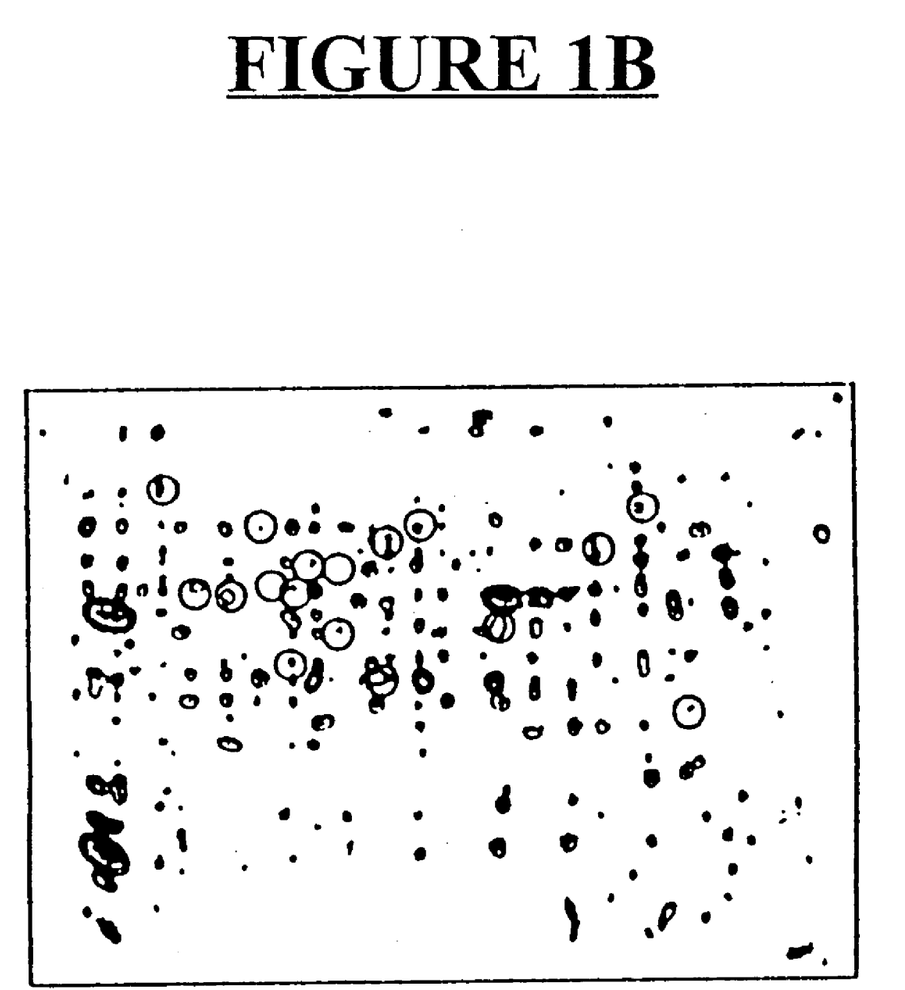
Figure 1C:
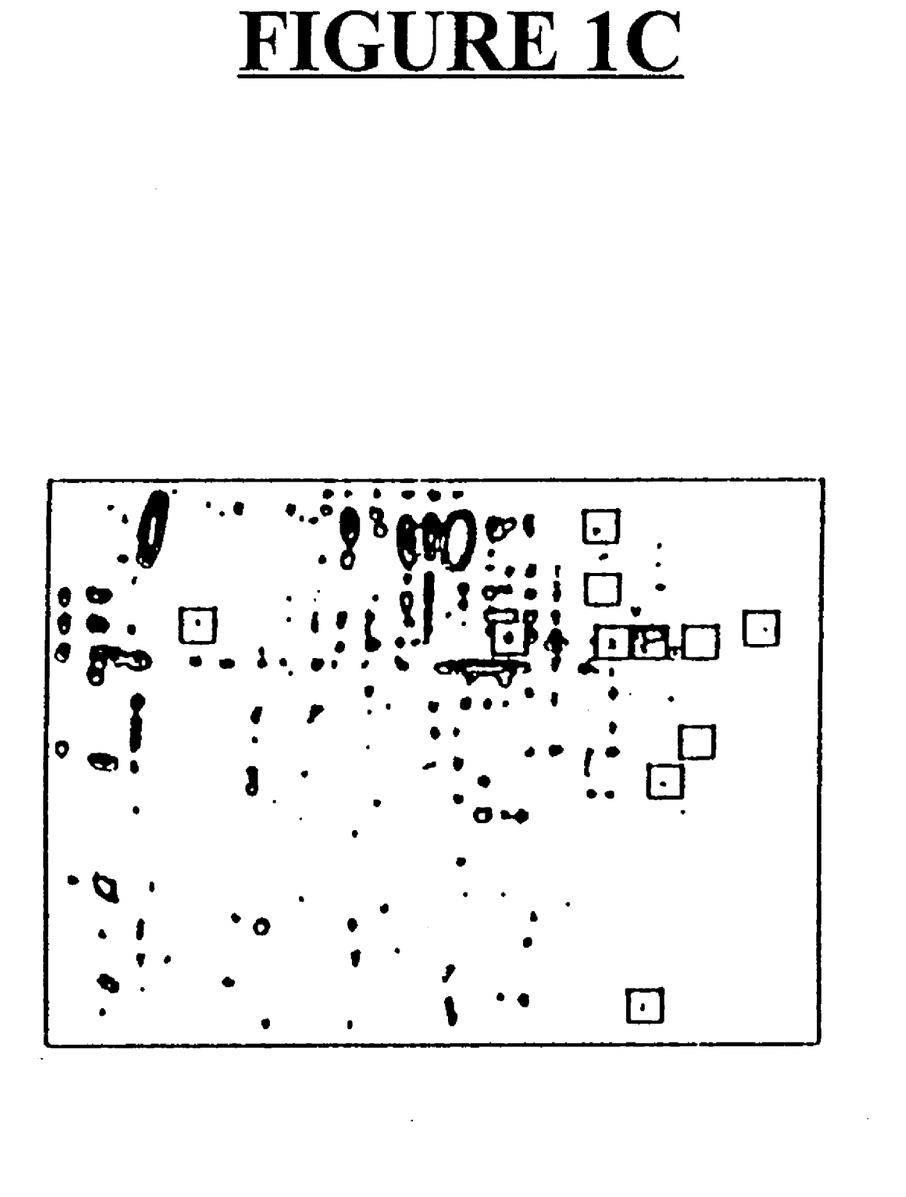
Figure 1D:
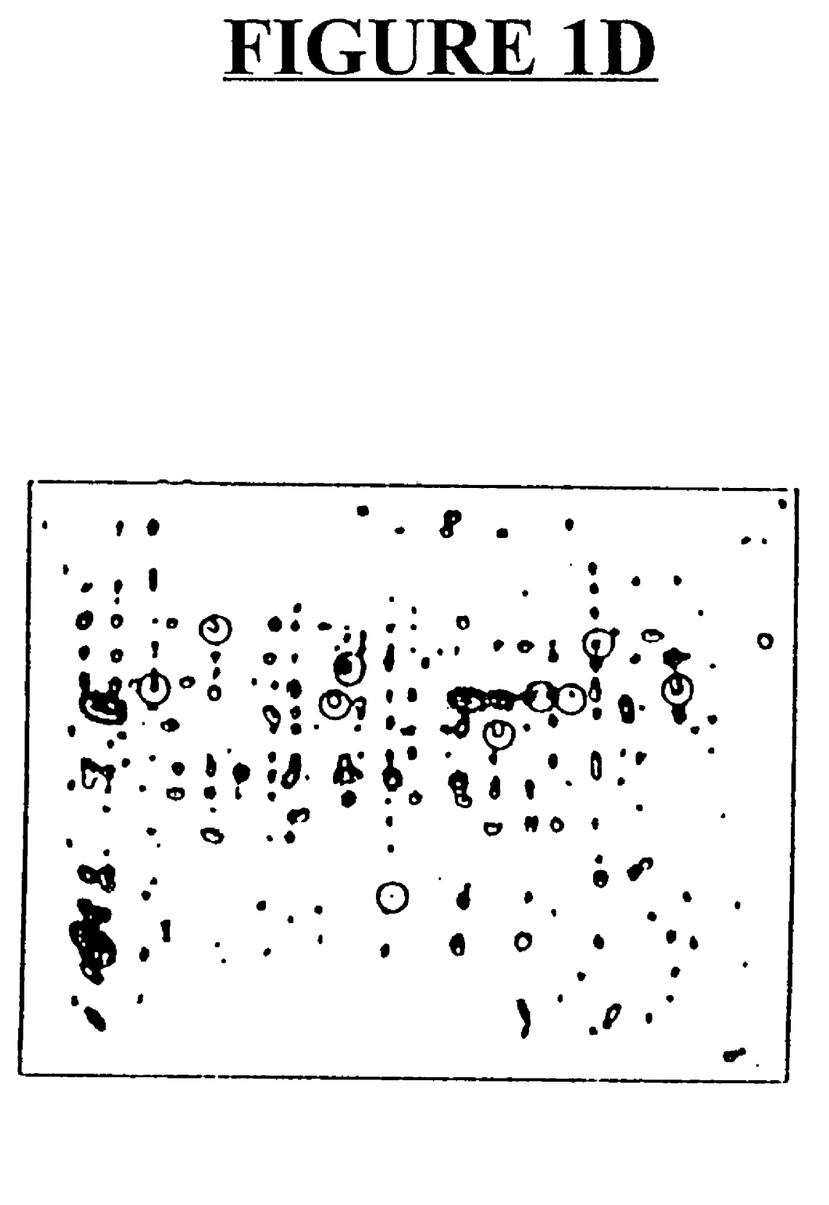
Figure 1E:
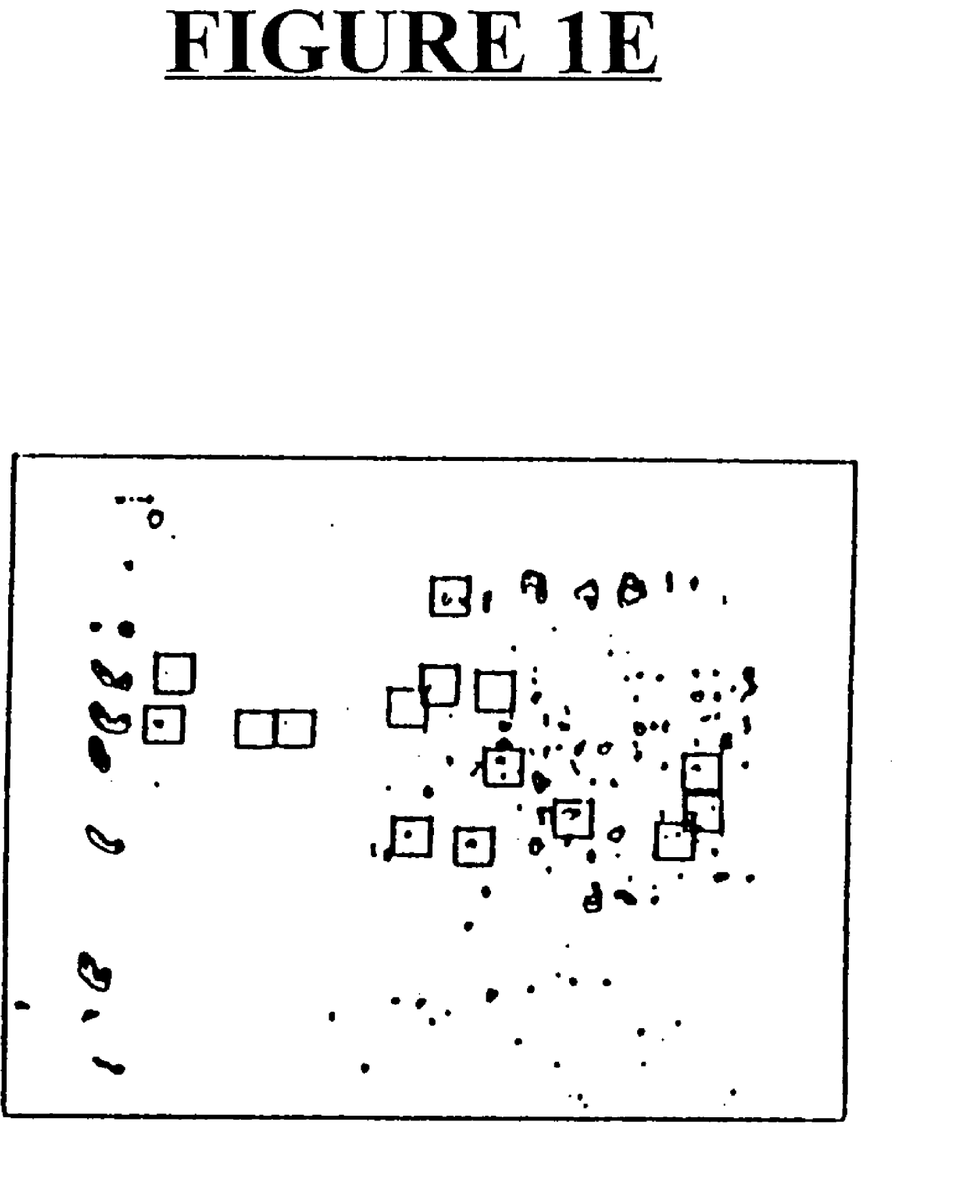
Figure 1F:
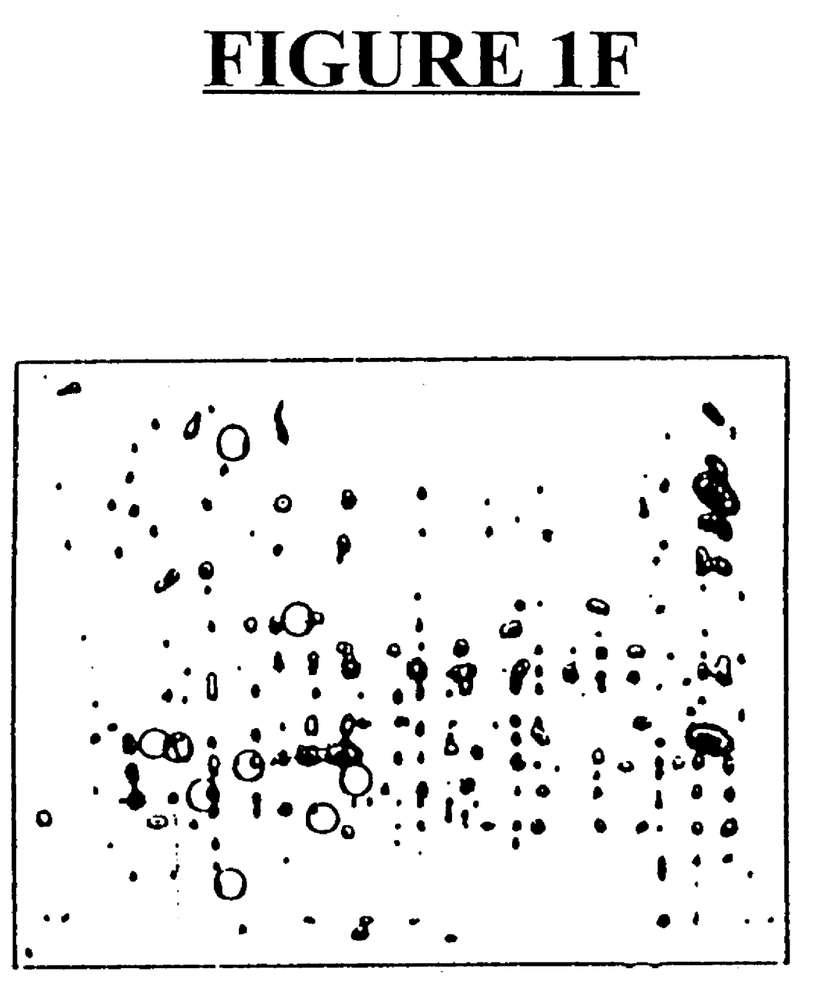
Figure 2A:
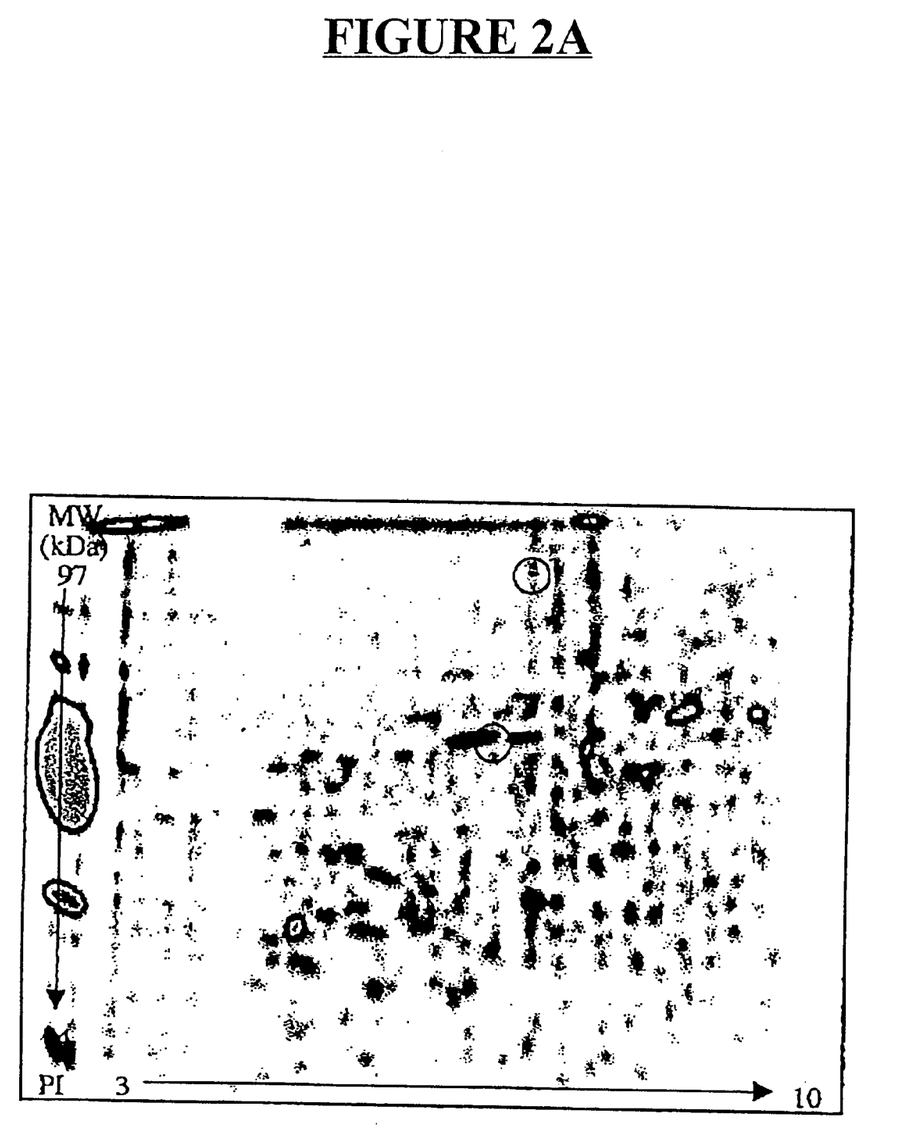
FIGS. 2(A) and 2(B) show composite gels produced from spots found on 75% of original 2D SDS-PAGE gels run using gill tissue from (A) control group *Mytilus edulis* and (B) mussels treated with 80 ppb $CuSO_4$ for 24 hours. Proteins absent in gels from all dosages of $CuSO_4$ (20, 40, 60, 80) on 100% of original gels are circled on the control image (A). Those proteins present in gels from all dosage levels of $CuSO_4$ (not just 80 ppb) and also on 100% of original gels are circled on the treatment image (B).
Figure 2B:
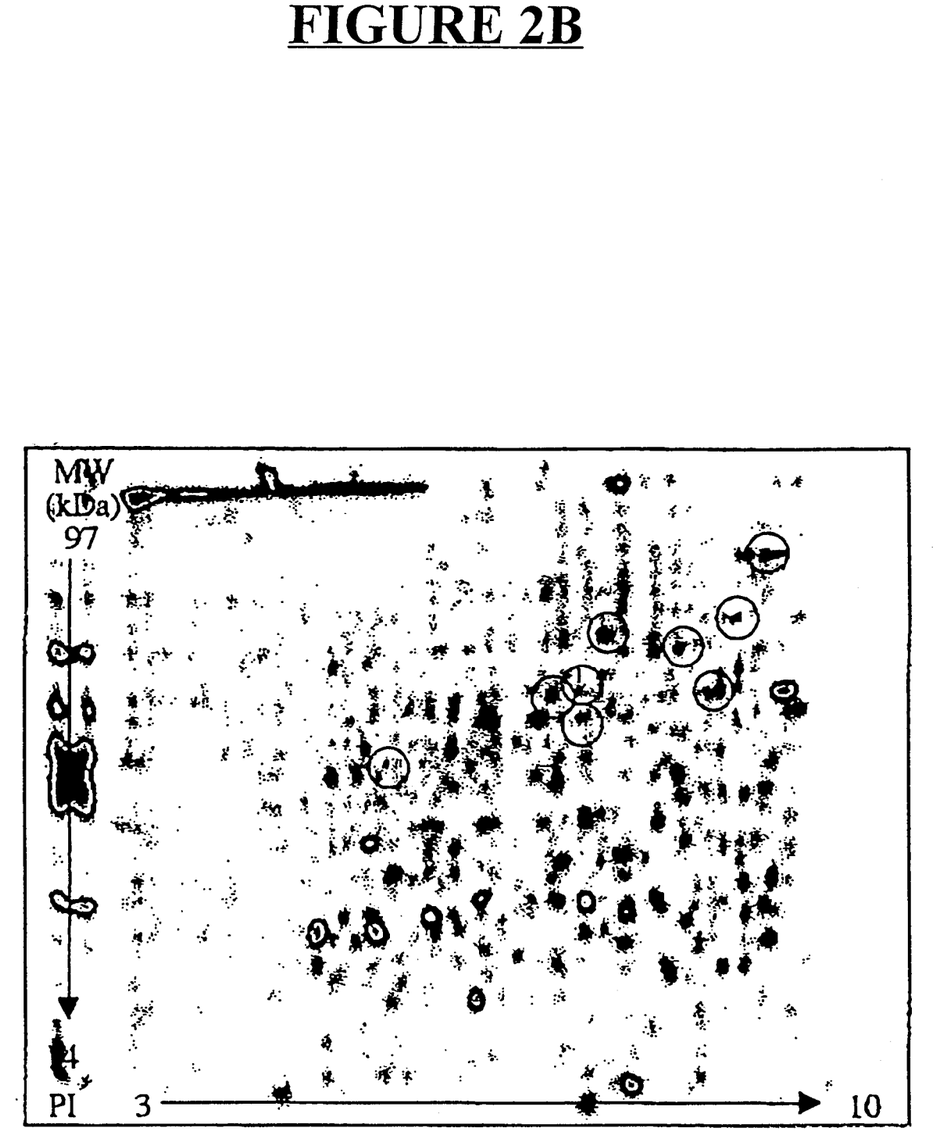

Protein expression changes common to all dosage levels were identified. When compared to controls, 11 protein spots were present and 2 spots absent at all treatment levels (20, 40, 60, 80 ppb $CuSO_4$) (see FIG. 2). The number of proteins specifically absent at a single dosage level ranged from 14 protein spots at 20 ppb to 6 protein spots at 80 ppb. Induction of proteins varied with dosage decreasing between 20 ppb and 40 ppb and increasing again at 60 ppb (see Table 2 and Table 3).

The ratio method of determining lysosomal damage using a neutral red retention assay requires no complex cell separations, requires few cells per sample, produces quantitative data and is not limited by the need for assessment while cells are living.

Changes in protein expression and lysosomal damage can be identified in the same individual exposed to low levels of copper for short periods of time. This study has shown that protein expression profiles of toxicant exposure can be identified at concentrations (20 ppb $CuSO_4$) below those causing significant lysosomal damage (60 ppb $CuSO_4$). Proteins common to all copper concentrations were isolated as were signature proteins specific to each dosage level. Protein indicators have already been shown to be specific to stressors using these methods. Bradley (1996); Gonzalez et al. (1994). Given the protein expression signatures for different concentrations, protein expression can be linked to cellular damage, statistically, using existing data and functionally when key proteins are identified. Wilkens et al. (1997).

TABLE 2

Lysosomal Damage and Protein Changes From Gill Tissue of *Mytilus edulis* treated with increasing levels of $CuSO_4$

| Dosage (ppb $CuSO_4$)[1] | 0 | 20 | 40 | 60 | 80 | All Dosages |
|---|---|---|---|---|---|---|
| Lysosomal Destabilization Ratio | 0.18 ± 0.01 | 0.20 ± 0.03 | 0.21 ± 0.02 | 0.27 ± 0.02 | 0.32 ± 0.11 | |
| Key Protein Changes[2] | — | 27 | 14 | 19 | 10 | 13 |

[1]All animals were exposed to $CuSO_4$ for 24 hrs.
[2]The number of key proteins found to be present and absent in each treatment specifically when compared to the control group and all other treatment groups.

TABLE 3

Proteins from Gill Tissue of *Mytilus Edulis* Treated With Increasing Levels of CuSO$_4$

| Treatment with CuSO$_4$ Present/Absent on Treatment Gels | MELANIE ID Feature Number | Estimated Molecular Weight (KiloDaltons) | Estimated Isoelectric Focusing Point |
|---|---|---|---|
| 20 ppb CuSO$_4$ Present | 76 | 169.4 | 4.4 |
| | 82 | 167.2 | 3.2 |
| | 106 | 148.0 | 4.3 |
| | 184 | 109.4 | 4.2 |
| | 293 | 77.3 | 8.6 |
| | 345 | 65.1 | 8.2 |
| | 415 | 58.6 | 6.0 |
| | 491 | 51.5 | 5.8 |
| | 527 | 48.4 | 5.6 |
| | 592 | 42.0 | 6.2 |
| | 685 | 35.7 | 6.3 |
| | 967 | 20.0 | 4.3 |
| 20 ppb CuSO$_4$ Absent | 184 | 80.0 | 5.9 |
| | 327 | 58.2 | 6.5 |
| | 331 | 57.4 | 10.0 |
| | 350 | 55.8 | 8.6 |
| | 371 | 52.6 | 9.2 |
| | 419 | 45.6 | 10.0 |
| | 446 | 43.3 | 5.5 |
| | 540 | 38.9 | 9.6 |
| | 552 | 37.6 | 10.0 |
| | 582 | 36.8 | 5.8 |
| | 605 | 35.7 | 8.4 |
| | 626 | 34.3 | 5.5 |
| | 697 | 30.9 | 4.8 |
| | 737 | 29.2 | 9.3 |
| | 738 | 29.0 | 5.0 |
| 40 ppb CuSO4 Present | 388 | 46.2 | 5.5 |
| | 396 | 44.7 | 6.2 |
| 40 ppb CuSO4 Absent | 25 | 169.1 | 5.5 |
| | 48 | 149.1 | 9.5 |
| | 170 | 85.9 | 7.9 |
| | 255 | 63.7 | 3.9 |
| | 332 | 57.4 | 7.0 |
| | 366 | 53.2 | 5.8 |
| | 375 | 52.9 | 7.9 |
| | 391 | 51.5 | 4.4 |
| | 460 | 42.5 | 8.1 |
| | 589 | 36.2 | 9.3 |
| | 772 | 27.6 | 5.8 |
| | 776 | 27.5 | 9.3 |
| 60 ppb CuSO4 Present | 159 | 103.2 | 8.3 |
| | 197 | 89.0 | 4.9 |
| | 314 | 62.6 | 4.1 |
| | 392 | 55.2 | 6.1 |
| | 400 | 52.7 | 4.5 |
| | 406 | 53.4 | 4.9 |
| | 472 | 44.5 | 7.8 |
| | 809 | 25.9 | 8.0 |
| | 878 | 20.0 | 7.3 |
| | 907 | 17.9 | 4.4 |
| | 908 | 18.1 | 4.7 |
| | 915 | 17.2 | 7.4 |
| 60 ppb CuSO4 Absent | 74 | 127.3 | 3.8 |
| | 77 | 124.4 | 4.9 |
| | 88 | 119.4 | 4.8 |
| | 329 | 57.8 | 5.9 |
| | 524 | 39.8 | 3.8 |
| | 660 | 33.0 | 6.1 |
| | 699 | 31.0 | 7.6 |
| 80 ppb CuSO4 Present | 164 | 95.8 | 10.0 |
| | 210 | 80.6 | 3.5 |
| | 226 | 75.5 | 10.0 |
| | 459 | 44.4 | 4.0 |
| 80 ppb CuSO4 Absent | 167 | 86.5 | 3.6 |
| | 230 | 66.0 | 3.6 |
| | 343 | 56.6 | 3.3 |
| | 439 | 44.1 | 4.4 |
| | 577 | 37.7 | 7.1 |
| | 748 | 29.0 | 5.3 |
| All doses CuSO4 Present | 83 | 133.1 | 3.7 |
| | 193 | 84.0 | 4.0 |
| | 248 | 67.9 | 4.5 |
| | 325 | 58.4 | 4.7 |
| | 329 | 57.7 | 4.3 |
| | 333 | 58.6 | 5.5 |
| | 390 | 52.9 | 5.5 |
| | 227 | 73.7 | 5.2 |
| | 296 | 61.2 | 5.5 |
| | 339 | 57.9 | 5.7 |
| | 482 | 42.2 | 7.4 |
| All doses CuSO4 Absent | 60 | 138.9 | 5.8 |
| | 384 | 52.6 | 6.2 |

Example 3

The method of the invention was used to determine whether skin irritation could be predicted or diagnosed. A "band-aid" type patch was used to sample exuded proteins from the arms of test individuals. The patch was removed and dermal tissue samples were taken from various treatments. PES were then isolated from the dermal tissue samples. Differences in PES were seen for varying treatments, including levels of hydration and exposures to surfactants.

Thus, the method of the invention can be used to evaluate potential adverse effects of many substances, including those exposed to skin, e.g., dermatological compositions, baby care substances, cosmetics, lotions, creams, etc.

The present invention provides many uses to predict and prohibit potential toxicity; to diagnose and treat existing toxicity; and to determine and learn from past toxicity, including:

1. Human Testing

Identifying disease toxicity using comprehensive lab tests.

Recognizing early warning of cancer types using specific immunoassays or other protein capture technology.

Determining subclinical presence of disease or toxicity.

Determining potential adverse effects of pharmaceutical, cosmetic and other substances.

Portable kits for non-invasive testing of blood, urine, saliva or superficial tissue in physicians' office.

2. Plant and Animal Health Testing

Identifying disease resistant organisms in natural populations.

Diagnosing cause of illness.

Determining by early warning specific adverse conditions.

Portable kits, especially for blood or saliva tests or plant biopsies.

3. Environmental Testing

Identifying by Toxicity Identification Evaluation (T.I.E.) of specific chemicals or classes of chemicals.

Biomonitoring of air, soil, water, sediment quality.

Determining pesticide toxicity to non-target species.

Determining biological endpoint for environmental restoration.

Monitoring for mutagens and carcinogens using surrogates for humans.

Direct testing of humans for chemical or pathogen exposures.

Determining time since insult by observing kinds and amounts of proteins which have reappeared (environmental forensics).

Field kits for general and specific testing.

Predicting toxicity from proteins induced and suppressed well before clinical signs.

Numerous modifications and variations of the present invention are possible in light of the above teachings. In particular, it is noted that the identity of the host organism(s) involved for sampling, the nature of the environmental stressor(s), and the particular stress protein(s) assayed for, and assay protocol can be varied, given the abilities of the laboratory involved. It is therefore to be understood that within the scope of the appended claims, the invention may be practiced otherwise than as specifically described herein.

REFERENCES

1. Anderson, N. L. and N. G. Anderson, Proteome and proteomics: new technologies, new concepts and new words, Electrophoresis, 19:1853–61 (1998).
2. Arnold, R. J. and Reilly, J. P., Fingerprint matching of *E. coli* strains with matrix-assisted laser desorption/ionization time-of-flight mass spectrometry of whole cells using a modified correlation approach, Rapid Commun. Mass Spectrom., 12:630–6 (1998).
3. Blackstock et al., Proteomics: quantitative and physical proteins, Trends Biotech, 17:121–7 (1999).
4. Blom, et al., Unique and Overlapping Pollutant Stress Proteins of *Escherichia coli.*, Applied Environmental Microbiology, 58(1):331–334 (1992).
5. Bradley et al., Chemical Abstracts, Abstract No. 21161v, vol. 113 (1989).
6. Bradley, B. P. and J. B. Ward, Detection of a major stress protein using a peptide antibody, Mar. Environ. Res., 28:471–475 (1989).
7. Bradley, B. P. and J. B. Ward. A molecular mechanism of adaptation in an estuarine copepod., Neth. J. Sea Res., 30:1–6 (1989).
8. Bradley, B. P. 1992. Are the stress proteins specific indicators of exposure or effect?, Mar. Environ. Res., 34:85–88 (1992).
9. Bradley, B. P., Brown, D. C., Lamonte, T. N., Boyd, S. N. and O'Neill, M. C., Protein patterns and toxicity identification using artificial neural networks in "Biomarkers and Risk assessment, Amer. Soc. Testing and Materials STP1306, Philadelphia (1996).
10. Bradley, B. P., C. M. Gonzalez, J. A. Bond and B. E. Tepper, Complex mixtures analysis using protein expression as a qualitative and quantitative tool, Environ. Tox. and Chem., 13:1043–50 (1994).
11. Bradley et al., Protein Patterns and Toxicity Identification, Aquatic Toxicology and Risk Assessment, American Society for Testing and Material, Philadelphia (1996).
12. Claydon, M. A., Davey, S. N., Edwards-Jones, V. and Gurdon, P. E., The rapid identification of intact microorganisms using mass spectrometry, Nature Biotechnol., 14:1584–6 (1996).
13. Craig et al., Is hsp 70 the cellular thermometer?, Trends Biochem. Sci., 16:135–140 (1991).
14. Haag, A. M., Taylor, S. N., Johnston, K. H. and Cole, R. B., Rapid identification and specification of Haemophilus bacteria by matrix-assisted laser desorption/ionization time-of-flight mass spectrometry, J. Mass Spectrom, 33:750–6 (1996).
15. Hahn, G. M. and Li, C. G., Thermotolerance, thermoresistance, and thermosensitization, Stress Proteins in Biology and Medicine, Cold Spring Harbor Laboratory Press, Cold Spring Harbor, N.Y., pp. 79–100 (1990).
16. Herbert et al., Two-Dimensional Electrophoresis: The State of the Art and Future Directions, Proteome Research: New Frontiers in Functional Genomics, Springer-Verlag, Berlin (1997).
17. Hightower, L. E., Heat-shock proteins, chaperones and proteotoxicity, Cell, 66:191–197 (1991).
18. Humphrey-Smith, S. J., Cordwell and W. Blackstock, Proteome research: complementarity and limitations with respect to the RNA and DNA worlds, Electrophoresis, 18:1217–42 (1997).
19. Jellum et al., Two-Dimensional Electrophoresis for Determining Toxicity of Environmental Substances, Analytical Chemistry, 55: 2340–2344 (1983).
20. Kultz et al., Differences in Protein Patterns of Gill Epithelial Cells of the Fish *Gillichthys mirabilis* After Osmotic and Thermal Acclimation, J. Comp. Physiol., 166: 88–100 (1996).
21. Lindquist et al., The heat-shock proteins, Ann. Rev. Genet., 22:631–677 (1988).
22. McCarthy et al., Biological markers of environmental contamination, Biomarkers of Environmental Contamination, Lewis, Boca Raton, Fla., pp. 3–14 (1990).
23. Nover, L., Heat Shock Response, CRC, Boca Raton, Fla. (1991).
24. Nover, Heat Shock Response of Eukaryotic Cells (1984).
25. Parsell, D. A., J. Taulien and S. Lindquist. 1993. The role of heat-shock proteins in thermotolerance. Phil. Trans. R. Soc. Lond. B 339:279–286.
26. Ringwood, A. H., D. E. Conners and J. Hoguet, The Effects of Natural and Anthropogenic Stressors on Lysosomal Destablization in Oysters, *Crassosrra virginica*, Marine Ecology Progress Series (1998).
27. Sanders, B. M., Stress proteins in aquatic organisms: An environmental perspective, Crit. Rev. Toxicol., 23:49–75 (1993).
28. Stegmann et al., Molecular responses to environmental contamination: Enzyme and protein systems as indicators of chemical exposures and effects, Biomarkers: Biochemical, Physiological and Histological Markers of Anthropogenic Stress, Lewis, Boca Raton, Fla., pp. 235–310 (1992).
29. Van Bogelen, R. A., P. M. Keley and F. C. Neidhardt, Differential induction of heat shock, SOS and oxidation stress regulations and accumulation of nucleotides in *E. coli.*, J. Bacteriol., 169:26–32 (1987).
30. Welch, W. J., How cells respond to stress, Sci. Am., 268:56–64 (1993).
31. Welch, W. J., Heat shock proteins functioning as molecular choperones: Their roles in normal and stress cells, Phil. Trans. R. Soc. Lond B, 339:327–333 (1993).
32. Williams et al., Introduction to the Proteome, In Proteome Research: New Frontiers in Functional Genomics, Springer-Verlag, Berlin (1997).
33. Winston, G. W., M. N. Moore, I. Staatsburg and M. A. Kirchin, Decreased Stability of Digestive Gland Lysosomes from the Common Mussels *Alytilus edulis* L., In Vitro Generation of Oxygen-Free Radicals, Arch. Environ. Contam. Toxicol., 21: 401408 (1991).

What is claimed is:

1. A method of determining the expression and suppression of proteins specific to a stressor so as to develop a single dynamic index of stress, the method comprising:

(a) determining base control level protein expression of an organism or population of organisms;

(b) exposing said organism or population of organisms a first time to said stressor; said organism or population of organisms expressing a first set of one or more proteins and suppressing a second set of one or more proteins in response to stress induced by said stressor, wherein an amount of said stressor correlates to (1) the amounts of expressed proteins in said first set of one or more proteins and (2) the amounts of suppressed proteins in said second set of one or more proteins;

(c) determining said first set of one or more proteins and said second set of one or more proteins expressed and suppressed by said organism, respectively, upon being exposed to said stressor;

(d) identifying specific subsets of proteins expressed and suppressed for the stressor, said subsets of proteins being unique to said stressor and distinct from all other stressors likely to be present;

(e) weighting said subsets of proteins individually to maximize the power of discrimination in providing a weighted protein expression signature;

(f) exposing said organism or population of organisms a second time, or a second organism or population of organisms a first time, to said stressor, said stressor being at an amount greater than an amount used previously; and (g) repeating step (c) to statistically obtain stressor induced weighted protein expression signatures to maximally distinguish concentrations or intensities of response to said stressor over a range of concentrations or intensities, wherein a single dynamic index of stress is developed using the weights of the amounts of proteins determined over a range of protein expression for an organism.

2. The method of claim 1, further comprising:

repeating steps (e) and (f) one or more times to obtain subsequent stressor induced protein expression signatures.

3. The method of claim 1, wherein said proteins in (1) and (2) are weighted using discriminant function analysis or artificial neural networks.

4. The method of claim 1, wherein said weighted protein expression signature is determined by comparing sets of proteins observed sequentially in one individual organism.

5. The method of claim 1, wherein said base level of proteins is determined after recovery of said organism or population of organisms from said stress, by comparison of protein profiles before and after recovery.

6. The method of claim 1, wherein said stress is due to any biological, chemical or physical factor causing changes at the protein level, said changes being determined as expression or suppression of protein levels when compared to said single dynamic index.

7. The method of claim 1, wherein said method of determining the expression and suppression of proteins specific to a stressor provides an early warning of disease indicator, said early warning being indicated by expression or suppression of protein levels when compared to said single dynamic index.

8. The method of claim 1, wherein said method of determining the expression and suppression of proteins specific to a stressor provides a forensic indicator, said forensic indicator being identifiable as an expression or suppression of protein levels when compared to said single dynamic index.

9. A stressor induced protein expression signature prepared by the method of claim 1.

* * * * *